United States Patent
Lv et al.

(10) Patent No.: US 11,059,773 B2
(45) Date of Patent: Jul. 13, 2021

(54) TYPE-B FENOLAMINE CRYSTAL FORM, PREPARATION METHOD, COMPOSITION AND USE THEREOF

(71) Applicants: INSTITUTE OF MATARIA MEDICA, CHINESE ACADEMY OF MEDICAL SCIENCES, Bejing (CN); SHIJIAZHUANG YILING PHARMACEUTICAL CO., LTD., Shijiazhuang (CN)

(72) Inventors: Yang Lv, Shijiazhuang (CN); Shiying Yang, Shijiazhuang (CN); Gengtao Liu, Shijiazhuang (CN); Dan Zhang, Shijiazhuang (CN); Xiuqi Bao, Shijiazhuang (CN); Ping Xie, Shijiazhuang (CN)

(73) Assignees: INSTITUTE OF MATARIA MEDICA, CHINESE ACADEMY OF MEDICAL SCIENCES, Bejing (CN); SHIJIAZHUANG YILING PHARMACEUTICAL CO., LTD., Shijiazhuang (CN)

(*) Notice: Subject to any disclaimer, the term of this patent is extended or adjusted under 35 U.S.C. 154(b) by 42 days.

(21) Appl. No.: 16/629,554

(22) PCT Filed: Sep. 7, 2018

(86) PCT No.: PCT/CN2018/104573
§ 371 (c)(1),
(2) Date: Jan. 8, 2020

(87) PCT Pub. No.: WO2019/011349
PCT Pub. Date: Jan. 17, 2019

(65) Prior Publication Data
US 2021/0078939 A1 Mar. 18, 2021

(30) Foreign Application Priority Data

Jul. 11, 2017 (CN) .......................... 201710560983.8

(51) Int. Cl.
*C07C 235/34* (2006.01)

(52) U.S. Cl.
CPC ........ *C07C 235/34* (2013.01); *C07B 2200/13* (2013.01)

(58) Field of Classification Search
None
See application file for complete search history.

(56) References Cited

FOREIGN PATENT DOCUMENTS

| CN | 1445211 A | 10/2003 |
| CN | 1308288 | * 4/2007 |
| WO | WO2019011350 A1 | 1/2019 |

OTHER PUBLICATIONS

English Machine Translation of (CN 1308288, Liang et al., 2007) (Year: 2007).*

(Continued)

*Primary Examiner* — Sudhakar Katakam
*Assistant Examiner* — Jennifer C Sawyer
(74) *Attorney, Agent, or Firm* — Foley & Lardner LLP

(57) ABSTRACT

The present invention discloses a type-B crystal form of fenolamine, a preparation method thereof, and a composition and use thereof, more particularly a type-B crystal form of the fenolamine compound (chemical name: trans-2-(2,5-dimethoxyphenyl)-3-(4-hydroxy-3-methoxyphenyl)-N-(4-hydroxyphenylethyl)acrylamide, a preparation method thereof, and a composition and use thereof. Specifically, the present invention discloses the presence of a solid of a type-B fenolamine crystal form in solid state; a method for preparing the solid of type-B crystal form; and use of the (Continued)

solid of the type-B fenolamine crystal form as a pharmaceutical active ingredient in the manufacture of a medicament for prevention and treatment of Parkinson's disease (PD), improvement of learning and memory disorder, and treatment of memory loss and Alzheimer's disease (AD).

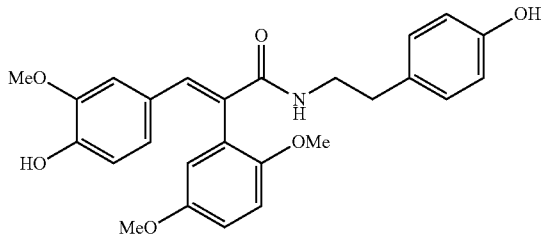

23 Claims, 10 Drawing Sheets

(56) References Cited

OTHER PUBLICATIONS

Bao et al., "FLZ Attenuates a-Synuclein-Induced Neurotoxicity by Activating Heat Shock Protein 70," Mol. Neurobiol., 13 pages (Jan. 7, 2016).
Bao et al., "Squamosamide Derivative FLZ Protected Tyrosine Hydroxylase Function in a Chronic MPTP/Probenecid Mouse Model of Parkinson's Disease," Naunyn-Schmiedeberg's Arch Pharmacol., vol. 388, pp. 549-556 (Feb. 13, 2015).
Bao et al., "The Novel Cyclic Squamosamide Derivative FLZ Improves Memory Deficits in Aged Mice and the Mechanisms," Chinese Journal of New Drugs, vol. 19, No. 10, pp. 867-872 (Dec. 31, 2010).
Cheng et al., "Squamosamide Derivative FLZ Protects Retinal Pigment Epithelium Cells from Oxidative Stress through Activation of Epidermal Growth Factor Receptor (EGFR)-AKT Signaling," Int. J. Mol. Sci., vol. 15, pp. 18762-18775 (Oct. 17, 2014).
Hou et al., "An in Vivo Microdialysis Study of FLZ Penetration through the Blood-Brain Barrier in Normal and 6-Hydroxydopamine Induced Parkinson's Disease Model Rats," BioMed Research International, 11 pages (Jun. 23, 2014).
Hou et al., "Quantitative determination and pharmacokinetic study of the novel anti-Parkinson's disease candidate drug FLZ in rat brain by high performance liquid chromatography-tandem mass spectrometry," Journal of Pharmaceutical and Biomedical Analysis, pp. 232-239 (Mar. 10, 2012).
International Search Report and Written Opinion, PCT/CN2018/104573 (dated Nov. 16, 2018).
International Search Report and Written Opinion, PCT/CN2018/104574 (dated Nov. 28, 2018) (WO2019011350A1—published Jan. 17, 2019).
Ji et al., "Studies on Total Synthesis of Squamosamide," Acta Pharmaceutica Sinica, vol. 28, No. 6, pp. 428-431 (Dec. 31, 1993).

Wu et al., "FLZ attenuates learning and memory deficits via suppressing neuroinflammation induced by LPS in mice," Journal of Asian Natural Products Research, 2015,17(3): 306-317.
Li et al., "Establishment of a HPLC method for preclinical pharmacokinetic study of the novel anti-Parkinson's disease candidate drug FLZ in rats," Biomed. Chromatogr. 2008, 22: 867-872.
Liu et al., "P-Glycoprotein Mediated Efflux Limits the Transport of the Novel Anti-Parkinson's Disease Candidate Drug FLZ across the Physiological and PD Pathological in Vitro BBB Models," PLOS One, 2014, 9(7): e102442.
English-language machine translation of Abstract for "Technical Guidelines for the Dissolution Test of Common Oral Solid Preparations," 15 pages (Oct. 2012).
Tai et al., "Inhibition of Src tyrosine kinase activity by squamosamide derivative FLZ attenuates neuroinflammation in both in vivo and in vitro Parkinson's disease models," Neuropharmacology, 2013, 75: 201-212.
Kong et al., "FLZ, a novel HSP27 and HSP70 inducer, protects SH-SY5Y cells from apoptosis caused by MPP," Brain Research, 2011, 1383: 99-107.
Bao et al., "Squamosamide derivative FLZ protected dopaminergic neuron by activating Akt signaling pathway in6-OHDA-induced in vivo and in vitro Parkinson's disease models," Brain Research, 2014, 1547: 49-57.
Bao et al., "FLZ Alleviates the Memory Deficits in Transgenic Mouse Model of Alzheimer's Disease via Decreasing Beta-Amyloid Production and Tau Hyperphosphorylation," PLOS One, 2013, 8 (11):| e78033.
Bao et al., "FLZ protects dopaminergic neuron through activating protein kinase B/mammalian target of rapamycin pathway and inhibiting RTP801 repression in Parkinson's disease models," Neuroscience. 2012, 202: 396-404.
Ye et al., "FLZ Inhibited Gamma-Secretase Selectively and Decreased as Mitochondrial Production in APP-SH-SY5Y Cells," Naunyn-Schmiedeberg's Arch Pharmacol., vol. 387, pp. 75-85 (Sep. 27, 2013).
Qin et al., "Anti-proliferative effects of the novel squamosamide derivative (FLZ) on HepG2 human hepatoma cells by regulating the cell cycle-related proteins are associated with decreased Ca2 /ROS levels," Chemico-Biological Interactions, 2011, 193: 246-253.
Zhang et al., "Squamosamide derivative FLZ protects dopaminergic neurons against inflammation-mediated neurodegeneration through the inhibition of NADPH oxidase activity," Journal of Neuroinflammation, 13 pages (May 28, 2008).
Zhang et al., "The novel squamosamide derivative (compound FLZ) attenuated 1-methyl, 4-phenyl-pyridinium ion (MPPt)-induced apoptosis and alternations of related signal transduction in SH-SY5Y cells," Neuropharmacology, pp. 423-429 (Aug. 2006).
Zhang et al., "The novel squamosamide derivative FLZ protects against 6-hydroxydopamine-induced apoptosis through inhibition of related signal transduction in SH-SY5Y cells," European Journal of Pharmacology, 6 pages (Nov. 16, 2006).
Chinese Search Report for CN 201710560983.8 dated Jul. 30, 2020.
Fang et al, "Protective effects of compound FLZ, a novel synthetic analogue of squamosamide, on B-amyloid-induced rat brain mitochondrial dysfunction in vitro," Acta Pharmacol Sin, May 2009, pp. 522-529.
First Chinese Office Action for CN 201710560983.8 dated Jul. 30, 2020.

\* cited by examiner

TYPE-B FENOLAMINE CRYSTAL FORM, PREPARATION METHOD, COMPOSITION AND USE THEREOF

CROSS-REFERENCE TO RELATED APPLICATIONS

This application is a National Stage Application of PCT/CN2018/104573, filed Sep. 7, 2018, which claims the benefit of and priority to Chinese Patent Application No. 201710560983.8, filed Jul. 11, 2017, the entire contents of which are incorporated herein by reference.

TECHNICAL FIELD

The present invention relates to the discovery of the presence of a solid state form of type-B crystal form of fenolamine in solid state, and to a method for preparing the type-B crystal form. The present invention relates to a pharmaceutical composition comprising the type-B crystal form of fenolamine and a mixed crystal form having any ratio of the type-B crystal form. The present invention also relates to use of the crystalline fenolamine species as a pharmaceutical active ingredient in the manufacture of a medicament for prevention and treatment of Parkinson's disease (PD), improvement of learning and memory disorder, and treatment of memory loss and Alzheimer's disease (AD).

BACKGROUND

Fenolamine (chemical name: trans-2-(2,5-dimethoxyphenyl)-3-(4-hydroxy-3-methoxyphenyl)-N-(4-hydroxyphenylethyl) acrylamide) has a molecular structure as follows:

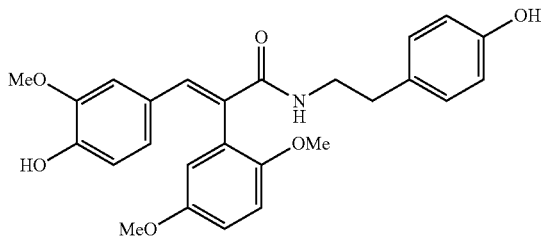 [SMILES: COc1ccc(OC)c(/C(=C\c2ccc(O)c(OC)c2)C(=O)NCCc2ccc(O)cc2)c1]

Fenolamine (FLZ) is a derivative of squqmosamide, the compound structure of which has been disclosed in Chinese patent Publication No. CN 1445211 in which is described "new squqmosamide derivative and its preparation method, pharmaceutical composition and use"[1] invented by the Institute of Materia Medica, Chinese Academy of Medical Sciences. Herein, Example 24 implicates a method for synthesizing fenolamine in which was obtained by recrystallization from chloroform as solvent and the fenolamine solid sample was determined as a type-F crystal form containing crystalline chloroform molecules by powder X-ray diffraction analysis.

Eighteen articles concerning fenolamine were found upon literature search[2-19], but these articles all report on the pharmacological effects or pharmacokinetic studies of fenolamine, but do not involve preparation method and crystal form substance.

No patent or literature report on other crystal forms of fenolamine have been found by domestic and foreign patents and literature searches.

The inventors of present invention have discovered a new solid state of a type-B crystal form of fenolamine and a preparation method different from those reported in the above patents or literatures, determined the characteristics of changes in crystal forms in the blood and blood concentration after the solid of the type-B fenolamine crystal form is taken up by oral administration, and found that the solid of the type-B fenolamine crystal form has good stability.

The objective of the studies in the present invention is to seek and discover the species and state characteristics of crystalline solid substances at the level of raw materials for active ingredients of a medicament, by using crystal form screening techniques and crystal form biological activity evaluation techniques and starting from the study on the state of the present fenolamine crystalline solid, and associate the crystalline substances with pharmacodynamic studies, so as to provide fundamental scientific data for finding, discovering and developing a superior medicinal fenolamine crystalline solid having an optimal clinical efficacy, and also to provide a scientific basis for seeking domestic or international patent protection of proprietary inventions based on the pharmaceutical raw material of the fenolamine solid.

SUMMARY OF THE INVENTION

A technical problem to be solved by the invention is to provide fenolamine present in a new solid state and characterization thereof, that is, a type-B fenolamine crystal form.

It was found in preliminary studies that fenolamine may easily combine with solvent molecules such as acetone (type-A crystal form), ethanol (type-B crystal orm), isopropanol (type-C crystal form), ethyl acetate (type-E crystal form), and chloroform (type-F crystal form) to form solvates in different crystal forms during re-crystallization. The type-B fenolamine crystal form according to the present application is an ethanolate formed from fenolamine and ethanol, which belongs to a special solvate, i.e., a non-stoichiometric solvate. The ratio of compound molecules to solvent molecules in such a solvate is often not an integer ratio, wherein the solvent molecules occupy certain positions in the lattice whereas the increase or decrease of the number of the solvent molecules has little effect on the lattice arrangement. Therefore, the type-B crystal form is a crystal form group including a series of subtypes, and there is an identical or similar spatial lattice pattern among different subtypes except for the difference in the number of crystallized ethanol included. The crystal forms including various number of crystallized ethanol are distinguished as type-$B_1$ crystal form, type-$B_2$ crystal form, type-$B_3$ crystal form, . . . and type-$B_n$ crystal form.

Further, from single crystal X-ray diffraction data of type-B fenolamine crystal form, it can be found that the different contents of crystallized ethanol has an impact on the powder spectrum of the pure fenolamine crystal form product: with the decrease of the content of crystallized ethanol contained in type-B crystal form samples, the diffraction peak positions are essentially consistent in theoretical powder diffraction spectra, but the intensities of the diffraction peaks vary, with the most prominent change in relative intensities of the diffraction peaks with 2θ values of 10.5°, 16.0°, and 24.2°, wherein the intensity of the diffraction peak with the 2θ value of 10.5° increases and the intensity of the diffraction peak with the 2θ value of 24.2° decreases as the content of crystallized ethanol contained in type-B crystal form samples decreases.

The second technical problem to be solved by the present invention is to provide a method for preparing a solid of the type-B fenolamine crystal form.

The third technical problem to be solved by the present invention is to provide a solid medicament containing a pure substance of fenolamine of the type-B crystal form or a mixed crystal form having any ratio of the type-B crystal form, and a composition thereof.

The fourth technical problem to be solved by the present invention is to provide a pharmaceutical composition having the solid of the type-B fenolamine crystal form as a pharmaceutically active ingredient in a daily dose of 10 to 3000 mg. The pharmaceutical composition includes a tablet, a capsule, a pill, an injection, a sustained release or a controlled release preparation.

The fifth technical problem to be solved by the present invention is to provide the use of the solid of the type-B fenolamine crystal form in the manufacture of a medicament for prevention and treatment of Parkinson's disease (PD), improvement of learning and memory disorder, and treatment of memory loss and Alzheimer's disease (AD).

The invention adopts the following technical solutions in order to the above technical problems:

1. Morphological Characteristics of Type-B Fenolamine Crystal Form Samples:

1.1 The present invention relates to a solid of a type-B fenolamine crystal form which shows a symmetry of a monoclinic crystal system upon single crystal X-ray diffraction analysis, with a Cc space group and unit cell parameters of: a=31.18 Å, b=8.92 Å, c=22.50 Å, α=γ=90°, β=128.4°, and an intracellular molecule number Z=8, and includes crystallized ethanol molecules in unit cells in addition to fenolamine molecules. FIG. 1 shows the molecular arrangement in the type-B fenolamine crystal form, FIG. 2 shows the theoretical powder X-ray diffraction spectrum of a solid of the type-B fenolamine crystal form obtained from single crystal data calculation, FIGS. 3 to 4 show the theoretical powder X-ray diffraction spectrum of a solid of the type-B fenolamine crystal form with different amount of crystallized ethanol, respectively.

1.2 The present invention relates to a solid of a type-B fenolamine crystal form, wherein the type-B crystal form includes a series of subtypes and the ratio of fenolamine molecule to crystallized ethanol molecule is 1:0.5 to 1:0.1 in different subtypes, and wherein the subtype having a ratio of fenolamine molecule to crystallized ethanol molecule of 1:0.5 and the subtype having a ratio of fenolamine molecule to crystallized ethanol molecule of 1:0.2 are preferred, and the subtype having a ratio of fenolamine molecule to crystallized ethanol molecule of 1:0.2 is more preferred.

It can be understood that by the type-B crystal form including a series of subtypes according to the invention, it means there are possibly many subtypes of type-B crystal form, whereas the ratio of fenolamine molecule to crystallized ethanol molecule is different in each subtype.

In general, the fenolamine prepared is substantially composed of one of the subtypes, with the content of this subtype in mass percentage of more than 80%, preferably more than 85%, more preferably more than 90%, further preferably more than 95%, still further preferably more than 99%.

Furthermore, the fenolamine prepared may comprise other components in an impurity amount in addition to the above subtype, and said other components may include other subtypes of the type-B fenolamine crystal form than this subtype.

In some cases, a fenolamine mixture simultaneously containing multiple subtypes may be prepared in the present invention, that is, the fenolamine prepared is composed of a combination of different type-B fenolamine crystal form subtypes in a certain ratio.

It can be understood that by a ratio of fenolamine molecule to crystallized ethanol molecule of 1:0.5 to 1:0.1 in various subtypes according in the invention, it means the ratio of fenolamine molecule to crystal water molecule in various subtypes is independently 1:0.5 to 1:0.1, respectively.

1.3 The present invention relates to a solid of a type-B fenolamine crystal form which, by using powder X-ray diffraction analysis under the $CuK_\alpha$ radiation experimental conditions, has diffraction peaks at positions with 2-Theta values (°) or d values (Å) and diffraction peaks with relative intensity peak height values (Height %) or peak area values (Area %) as shown in the following table (FIG. 5, Table 1.1).

TABLE 1.1

Powder X-ray diffraction peak values of type-B fenolamine crystal form

| Peak | 2-Theta ± 0.2° | d(Å) ± 0.2 Å | Height % ± 10% | Area % ± 10% |
|---|---|---|---|---|
| 1 | 7.3 | 12.1 | 34 | 28 |
| 2 | 8.0 | 11.0 | 12 | 8 |
| 3 | 10.1 | 8.7 | 14 | 17 |
| 4 | 10.6 | 8.4 | 79 | 62 |
| 5 | 11.5 | 7.7 | 48 | 38 |
| 6 | 12.7 | 7.0 | 6 | 6 |
| 7 | 12.9 | 6.8 | 6 | 6 |
| 8 | 13.5 | 6.5 | 11 | 6 |
| 9 | 14.5 | 6.1 | 9 | 9 |
| 10 | 16.0 | 5.5 | 100 | 100 |
| 11 | 16.7 | 5.3 | 16 | 10 |
| 12 | 17.4 | 5.1 | 21 | 32 |
| 13 | 17.6 | 5.0 | 25 | 40 |
| 14 | 17.8 | 5.0 | 25 | 44 |
| 15 | 18.4 | 4.8 | 24 | 19 |
| 16 | 18.8 | 4.7 | 16 | 15 |
| 17 | 19.6 | 4.5 | 46 | 36 |
| 18 | 20.2 | 4.4 | 27 | 24 |
| 19 | 20.7 | 4.3 | 3 | 1 |
| 20 | 21.4 | 4.2 | 50 | 46 |
| 21 | 21.7 | 4.1 | 26 | 48 |
| 22 | 22.3 | 4.0 | 6 | 2 |
| 23 | 23.0 | 3.9 | 13 | 11 |
| 24 | 24.4 | 3.7 | 81 | 95 |
| 25 | 24.8 | 3.6 | 27 | 23 |
| 26 | 25.6 | 3.5 | 51 | 60 |
| 27 | 26.1 | 3.4 | 33 | 32 |
| 28 | 26.9 | 3.3 | 9 | 7 |
| 29 | 27.6 | 3.2 | 3 | 3 |
| 30 | 27.8 | 3.2 | 3 | 3 |
| 31 | 28.4 | 3.1 | 4 | 6 |
| 32 | 29.5 | 3.0 | 4 | 3 |
| 33 | 30.0 | 3.0 | 4 | 5 |
| 34 | 31.8 | 2.8 | 4 | 9 |
| 35 | 32.3 | 2.8 | 10 | 12 |
| 36 | 33.4 | 2.7 | 1 | 1 |
| 37 | 34.1 | 2.6 | 3 | 1 |
| 38 | 34.9 | 2.6 | 5 | 8 |
| 39 | 36.6 | 2.5 | 4 | 8 |
| 40 | 38.2 | 2.4 | 4 | 8 |
| 41 | 38.5 | 2.3 | 5 | 7 |
| 42 | 39.7 | 2.3 | 3 | 4 |
| 43 | 41.2 | 2.2 | 1 | 2 |
| 44 | 42.1 | 2.1 | 3 | 3 |
| 45 | 43.1 | 2.1 | 2 | 1 |
| 46 | 46.9 | 1.9 | 2 | 2 |
| 47 | 49.9 | 1.8 | 1 | 1 |

According to some particular embodiments of the present invention, by using powder X-ray diffraction analysis under the $CuK_\alpha$ radiation experimental conditions, the solid of the type-B fenolamine crystal form has diffraction peaks at positions with 2-Theta values (°) or d values (Å) and diffraction peaks with relative intensity peak height values (Height %) or peak area values (Area %) as shown in the following table (FIG. 6, Table 1.2).

TABLE 1.2

Powder X-ray diffraction peak values of type-B fenolamine crystal form

| Peak | 2-Theta ± 0.2° | d(Å) ± 0.2 Å | Height % ± 10% | Area % ± 10% |
|---|---|---|---|---|
| 1 | 7.3 | 12.2 | 23 | 16 |
| 2 | 8.0 | 11.0 | 9 | 4 |
| 3 | 10.5 | 8.4 | 62 | 40 |
| 4 | 11.4 | 7.7 | 37 | 23 |
| 5 | 12.6 | 7.0 | 6 | 4 |
| 6 | 12.9 | 6.8 | 5 | 4 |
| 7 | 13.4 | 6.6 | 7 | 3 |
| 8 | 14.4 | 6.1 | 7 | 5 |
| 9 | 16.0 | 5.5 | 92 | 73 |
| 10 | 16.7 | 5.3 | 11 | 6 |
| 11 | 17.4 | 5.1 | 26 | 24 |
| 12 | 17.7 | 5.0 | 37 | 32 |
| 13 | 18.3 | 4.8 | 24 | 15 |
| 14 | 18.7 | 4.7 | 17 | 11 |
| 15 | 19.5 | 4.5 | 49 | 32 |
| 16 | 20.1 | 4.4 | 30 | 21 |
| 17 | 21.3 | 4.2 | 66 | 54 |
| 18 | 21.7 | 4.1 | 29 | 53 |
| 19 | 22.2 | 4.0 | 6 | 2 |
| 20 | 22.9 | 3.9 | 15 | 10 |
| 21 | 24.3 | 3.7 | 100 | 100 |
| 22 | 24.7 | 3.6 | 32 | 39 |
| 23 | 25.5 | 3.5 | 70 | 62 |
| 24 | 26.0 | 3.4 | 49 | 37 |
| 25 | 26.8 | 3.3 | 13 | 7 |
| 26 | 27.6 | 3.2 | 7 | 4 |
| 27 | 28.4 | 3.1 | 7 | 5 |
| 28 | 29.4 | 3.0 | 5 | 4 |
| 29 | 29.9 | 3.0 | 5 | 7 |
| 30 | 30.1 | 3.0 | 6 | 4 |
| 31 | 31.9 | 2.8 | 5 | 8 |
| 32 | 32.2 | 2.8 | 16 | 12 |
| 33 | 33.0 | 2.7 | 1 | 0 |
| 34 | 33.4 | 2.7 | 2 | 1 |
| 35 | 34.0 | 2.6 | 4 | 3 |
| 36 | 34.7 | 2.6 | 9 | 12 |
| 37 | 34.9 | 2.6 | 9 | 9 |
| 38 | 36.1 | 2.5 | 5 | 6 |
| 39 | 36.4 | 2.5 | 6 | 8 |
| 40 | 36.6 | 2.5 | 5 | 8 |
| 41 | 38.2 | 2.4 | 8 | 10 |
| 42 | 39.4 | 2.3 | 5 | 6 |
| 43 | 39.7 | 2.3 | 5 | 6 |
| 44 | 41.8 | 2.2 | 4 | 5 |
| 45 | 43.0 | 2.1 | 2 | 1 |
| 46 | 44.0 | 2.1 | 2 | 1 |
| 47 | 44.5 | 2.0 | 3 | 3 |
| 48 | 45.4 | 2.0 | 2 | 1 |
| 49 | 46.0 | 2.0 | 1 | 0 |
| 50 | 46.4 | 2.0 | 1 | 1 |
| 51 | 46.8 | 1.9 | 4 | 5 |
| 52 | 47.5 | 1.9 | 1 | 0 |
| 53 | 49.7 | 1.8 | 2 | 2 |
| 54 | 50.9 | 1.8 | 2 | 2 |
| 55 | 55.4 | 1.7 | 1 | 1 |

1.4 The present invention relates to a solid of a type-B fenolamine crystal form which, by using differential scanning calorimetry analysis, it shows one endothermic peak at 123° C.±3° C. and one at 130° C.±3° C. present respectively in the DSC pattern thereof in a range of 30 to 150° C. and at a heating rate of 3° C. per minute (FIG. 7).

1.5 The present invention relates to a solid of a type-B fenolamine crystal form which shows one weight loss peak in the range of 100 to 150° C. with a weight loss of 1.5% to 5.0% by using thermogravimetric analysis (FIG. 8).

1.6 The present invention relates to a solid of a type-B fenolamine crystal form, wherein by using attenuated total reflection Fourier infrared spectroscopy analysis, IR characteristic peaks are present at 3392, 3174, 3014, 2937, 2834, 2060, 1864, 1649, 1591, 1514, 1497, 1464, 1428, 1414, 1359, 1287, 1267, 1223, 1171, 1126, 1108, 1046, 952, 933, 907, 896, 857, 819, 773, 735, 710, 688, 643, 629, 562, 541, 514, 493, 452 cm$^{-1}$, wherein the allowable deviation of the IR characteristic peaks of is ±2 cm$^{-1}$ (FIG. 9).

1.7 A solid of mixed fenolamine crystal forms comprising the solid of the type-B fenolamine crystal form according to the invention in arbitrary proportion.

2. Features in Preparation of Type-B Fenolamine Crystal Form Samples and Mixed Crystal:

2.1 The present invention relates to a method for preparing a type-B fenolamine solid, wherein the solid of the type-B fenolamine crystal form is prepared by dissolving a fenolamine material completely with ethanol as sole solvent or a mixed solvent containing ethanol at a temperature of 15° C. to 80° C., followed recrystallization at ambient temperature of 4° C. to 80° C. and ambient humidity of 10% to 75% under normal pressure or vacuum experimental conditions.

2.2 The solid of mixed fenolamine crystal forms of the present invention is obtained by mixing the type-B fenolamine crystal form component prepared by the above method with solid of other fenolamine crystal forms in an arbitrary ratio by a conventional method.

3. Pharmaceutical Composition Containing a Component of Fenolamine Crystal Form(s), Dosing Regimen Features and Pharmaceutical Use:

3.1 The present invention relates to a pharmaceutical composition which comprises a type-B fenolamine crystal form and a pharmaceutically acceptable carrier.

3.2 The present invention relates to a pharmaceutical composition which comprises a solid of mixed fenolamine crystal forms and a pharmaceutically acceptable carrier.

3.3 The present invention relates to a pharmaceutical composition having a daily dose of fenolamine in the range of 10 to 3000 mg.

3.4 The present invention relates to a pharmaceutical composition, wherein the pharmaceutical composition is various tablets, capsules, pills, injection, sustained release preparations or controlled release preparations.

3.5 The present invention relates to the use of type-B fenolamine crystal form in the manufacture of a medicament for prevention and treatment of Parkinson's disease (PD), improvement of learning and memory disorders, and treatment of memory loss and Alzheimer's disease (AD).

3.6 The present invention relates to the use of mixed crystal forms comprising the type-B fenolamine crystal form at any ratio in the manufacture of a medicament for prevention and treatment of Parkinson's disease (PD), improvement of learning and memory disorders, and treatment of memory loss and Alzheimer's disease (AD).

3.7 The present invention relates to the use of a pharmaceutical composition in the manufacture of a medicament for prevention and treatment of Parkinson's disease (PD), improvement of learning and memory disorders, and treatment of memory loss and Alzheimer's disease (AD).

The present invention relates to a pharmaceutical composition comprising the type-B fenolamine crystal form component of the present invention or the solid of mixed fenolamine crystal forms of the present invention as an active ingredient. The pharmaceutical composition can be prepared according to methods well known in the art. The type-B fenolamine crystal form component of the present invention or the solid of mixed fenolamine crystal forms of the present invention can be prepared into any dosage forms suitable for human or animal use by combining with one or more pharmaceutically acceptable solid or liquid excipients and/or adjuvants. The content of the type-B fenolamine crystal form component of the present invention or the solid of mixed fenolamine crystal forms of the present invention is usually from 0.1 to 95% by weight in the pharmaceutical composition.

The type-B fenolamine crystal form component of the present invention or the solid of mixed fenolamine crystal forms of the present invention, or a pharmaceutical composition containing the same may be administered in a unit dosage form. The route of administration may be an enteral or parenteral route, such as oral, intravenous, intramuscular, subcutaneous, nasal, oral mucosa, ocular, lung and respiratory, skin, vaginal, rectal route, and the like.

The dosage form in which the present invention is administered is preferably a solid dosage form. The solid dosage form may be a tablet (including common tablet, enteric tablet, buccal tablet, dispersible tablet, chewable tablet, effervescent tablet, orally disintegrating tablet), a capsule (including hard capsule, soft capsule, enteric capsule), a granule, a powder, a pellet, a dropping pill, a suppository, a film, a patch, a gas (powder) spray, a spray, and the like.

The type-B fenolamine crystal form component of the present invention or the solid of mixed fenolamine crystal forms of the present invention can be prepared into a common preparation, a sustained release preparation, a controlled release preparation, a targeting preparation, and various microparticle delivery systems.

In order to formulate the type-B fenolamine crystal form component of the present invention or the solid of mixed fenolamine crystal forms of the present invention into a tablet, various excipients known in the art, including diluents, binders, wetting agents, disintegrants, lubricants, glidants, can be broadly used. The diluent may be starch, dextrin, sucrose, glucose, lactose, mannitol, sorbitol, xylitol, microcrystalline cellulose, calcium sulfate, calcium hydrogen phosphate, calcium carbonate and the like; the wetting agent may be water, ethanol, isopropanol or the like; the binder may be starch syrup, dextrin, syrup, honey, glucose solution, microcrystalline cellulose, gum arabic, gelatin syrup, sodium carboxymethyl cellulose, methyl cellulose, hydroxypropyl methyl cellulose, ethyl cellulose, acrylic resin, carbomer, polyvinylpyrrolidone, polyethylene glycol or the like; the disintegrant may be dry starch, microcrystalline cellulose, low-substituted hydroxypropyl cellulose, cross-linked polyvinylpyrrolidone, croscarmellose sodium, sodium carboxymethyl starch, sodium hydrogencarbonate and citric acid, polyoxyethylene sorbitan fatty acid ester, sodium dodecyl sulfate or the like; the lubricant and glidant can be talc, silica, stearate, tartaric acid, liquid paraffin, polyethylene glycol or the like.

Tablets may also be further formed into coated tablets, such as sugar coated tablets, film coated tablets, enteric coated tablets, or bilayer tablets and multi-layer tablets.

In order to prepare the dosage unit into a capsule, the active ingredient of type-B fenolamine crystal form component of the present invention or the solid of mixed fenolamine crystal forms of the present invention may be blended with a diluent or a glidant, and the mixture may be placed directly into a hard capsule or a soft capsule. Alternatively, the active ingredient of the type-B fenolamine crystal form component of the present invention or the solid of mixed fenolamine crystal forms of the present invention and a diluent, a binder, or a disintegrant may be first granulated or pelletized, and then placed into a hard capsule or a soft capsule. Various diluents, binders, wetting agents, disintegrants, and glidant materials for preparing the tablets of the type-B fenolamine crystal form component of the present invention or the solid of mixed fenolamine crystal forms of the present invention can also be used for preparing the capsules of the type-B fenolamine crystal form component of the present invention or the solid of mixed fenolamine crystal forms of the present invention.

In addition, colorants, preservatives, perfumes, flavoring agents, or other additives may also be added to the pharmaceutical preparations, if necessary.

The medicament or pharmaceutical composition of the present invention can be administered by any known administration method for the purpose of the administration and enhancing therapeutic effects.

The dosage of the pharmaceutical composition of the type-B fenolamine crystal form component of the present invention or the solid of mixed fenolamine crystal forms of the present invention may vary widely depending on the nature and severity of the disease to be prevented or treated, the individual conditions of the patient or animal, the route of administration and the dosage form and the like. The above dosages may be administered in one dosage unit or in separate dosage units depending on the clinical expertise of the physician and the dosage regimen including the use of other therapeutic means.

The type-B fenolamine crystal form component of the present invention or the solid of mixed fenolamine crystal forms of the present invention or the composition can be administered alone or in combination with other therapeutic drugs or symptomatic drugs. When there is a synergistic effect of the type-B fenolamine crystal form component of the present invention or the solid of mixed fenolamine crystal forms of the present invention and other therapeutic agents, the dosage thereof should be adjusted according to the actual situation.

4. Advantageous Technical Effects of the Invention:

4.1 Advantageous Feature in In Vitro Solubility of Type-B Fenolamine Crystal Form:

The solid of the type-B fenolamine crystal form of the invention has good solubility in six solvent systems imitating different pH environments in human body, and is superior to the type-F crystal form previously disclosed.

4.2 Advantageous Feature in Drug Safety of Type-B Fenolamine Crystal Form:

The solid of type-B fenolamine crystal form contains ethanol as crystallized solvent, which has little effect on human health, and therefore the type-B fenolamine crystal form solid has the advantageous feature in drug safety.

4.3 Stability of Type-B Fenolamine Crystal Form:

The solid of the type-B fenolamine crystal form of the invention has good stability. Results from experiments with influencing factors show that the type-B fenolamine crystal form solid is stable under conditions of high temperature, high humidity and light illumination, with transformation to subtypes having lower ethanol contents.

DETAILED DESCRIPTION OF THE INVENTION

The technical solutions of the present invention are described in details below with reference to the accompanying drawings and examples. However, the scope of protection of the present invention includes these but is not limited thereto.

Example 1

Preparation Method 1 of Type-B Fenolamine Crystal Form Sample:

1.46 kg of fenolamine was dissolved in 7.3 L of anhydrous ethanol by heating and stirring, then hot press-filtered into a crystallization kettle in a refining-drying-packing workshop, and allowed to stand at 20° C. overnight. The product was collected after filtration and dried under vacuum at 85° C. until there was no scent of ethanol (for about 48 hours, in this case the product was fenolamine with ½ crystallized ethanol). The obtained product was finely ground, sieved through an 80 mesh sieve, and dried under 10 mmHg vacuum at 100° C. for about 96 hours (the materials were turned over every 12 hours). The ethanol content was measured and when it was 1.7 to 2.4%, the product was qualified and 1.276 kg of the product was obtained. The product has an ethanol content of 2.0% as determined by gas chromatography, which is a subtype of the type-B fenolamine crystal form containing ⅕ crystallized ethanol; the powder X-ray diffraction spectrum, differential scanning calorimetric pattern, thermogravimetric diagram and infrared spectrum were shown in FIG. 5 and FIGS. 7-9.

Figure 1:
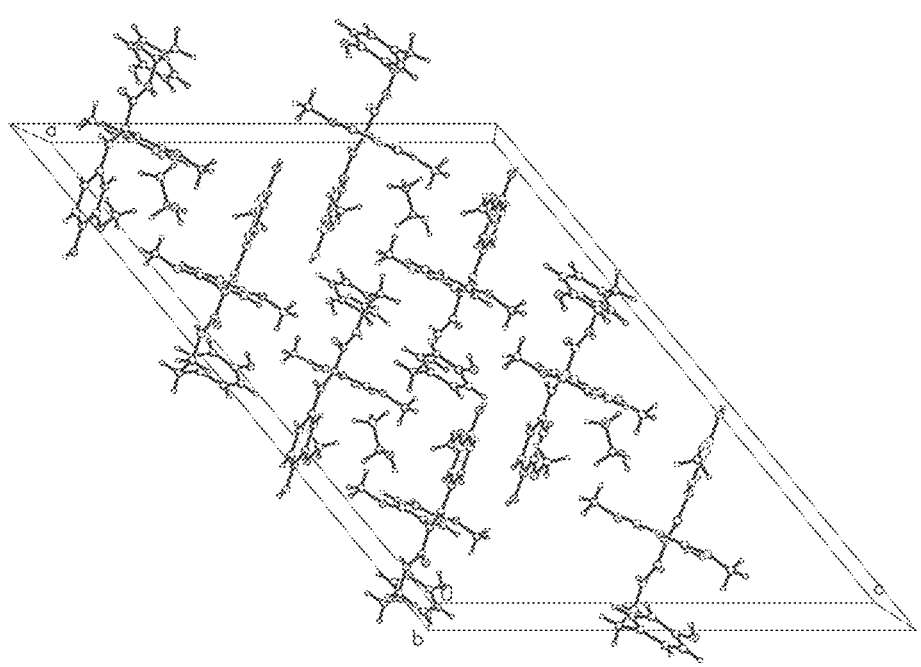
FIG. 1 is a graph of the molecular arrangement in a type-B fenolamine crystal form sample.
Figure 2:
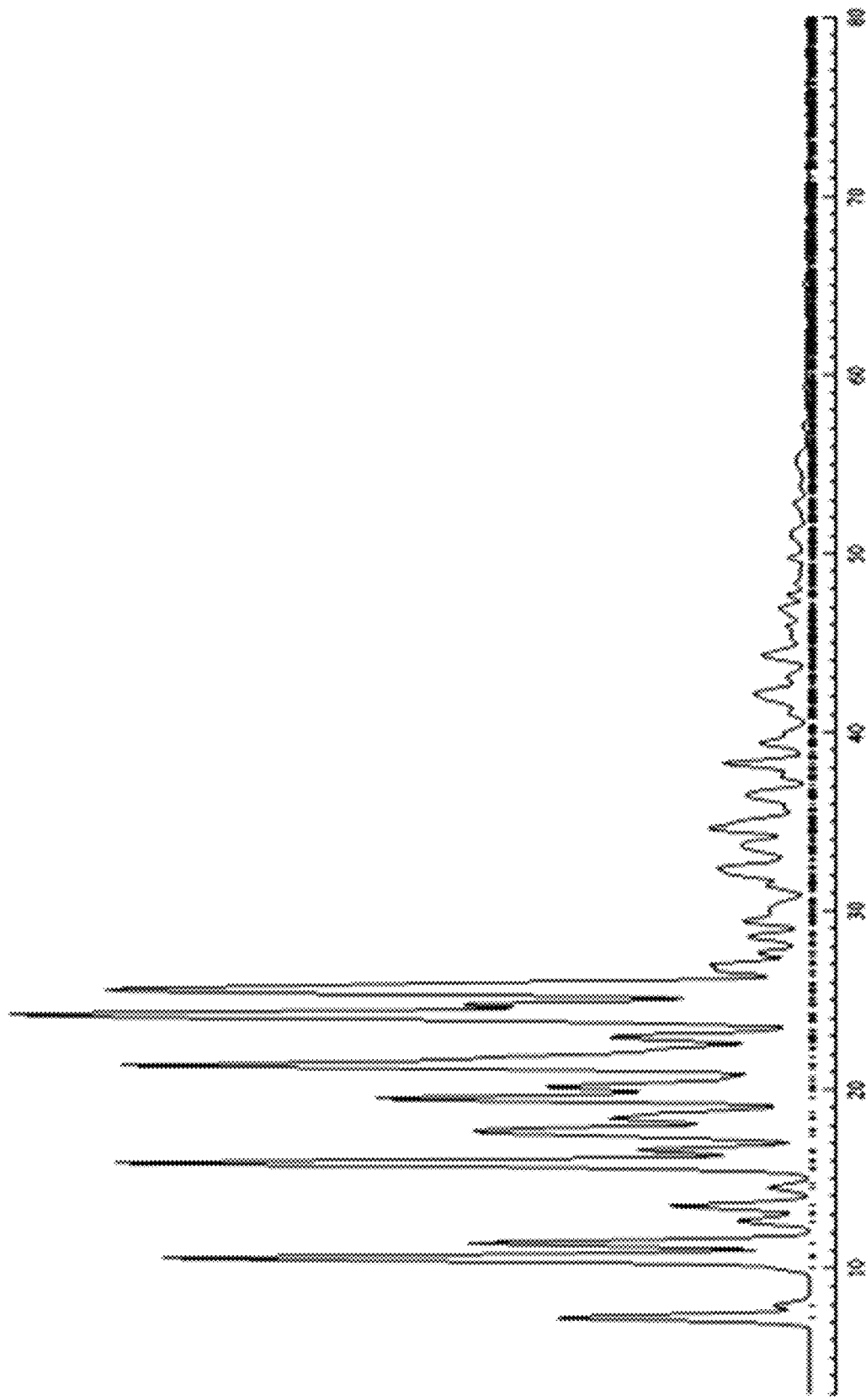
FIG. 2 is a theoretical powder X-ray diffraction spectrum of a type-B fenolamine crystal form sample (fenolamine: ethanol=2:1)
Figure 3:
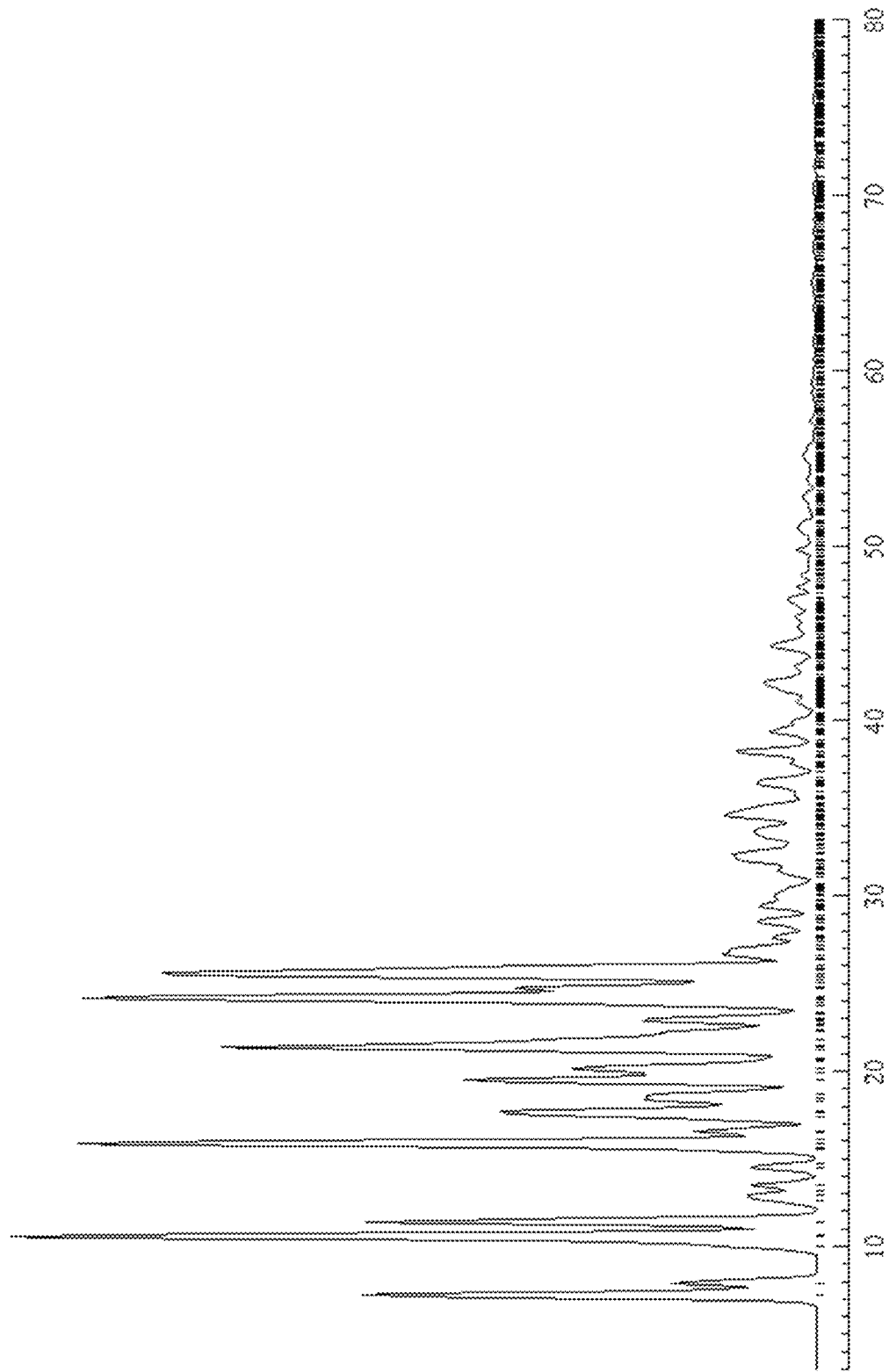
FIG. 3 is a theoretical powder X-ray diffraction spectrum of a type-B fenolamine crystal form sample (fenolamine: ethanol=4:1)
Figure 4:
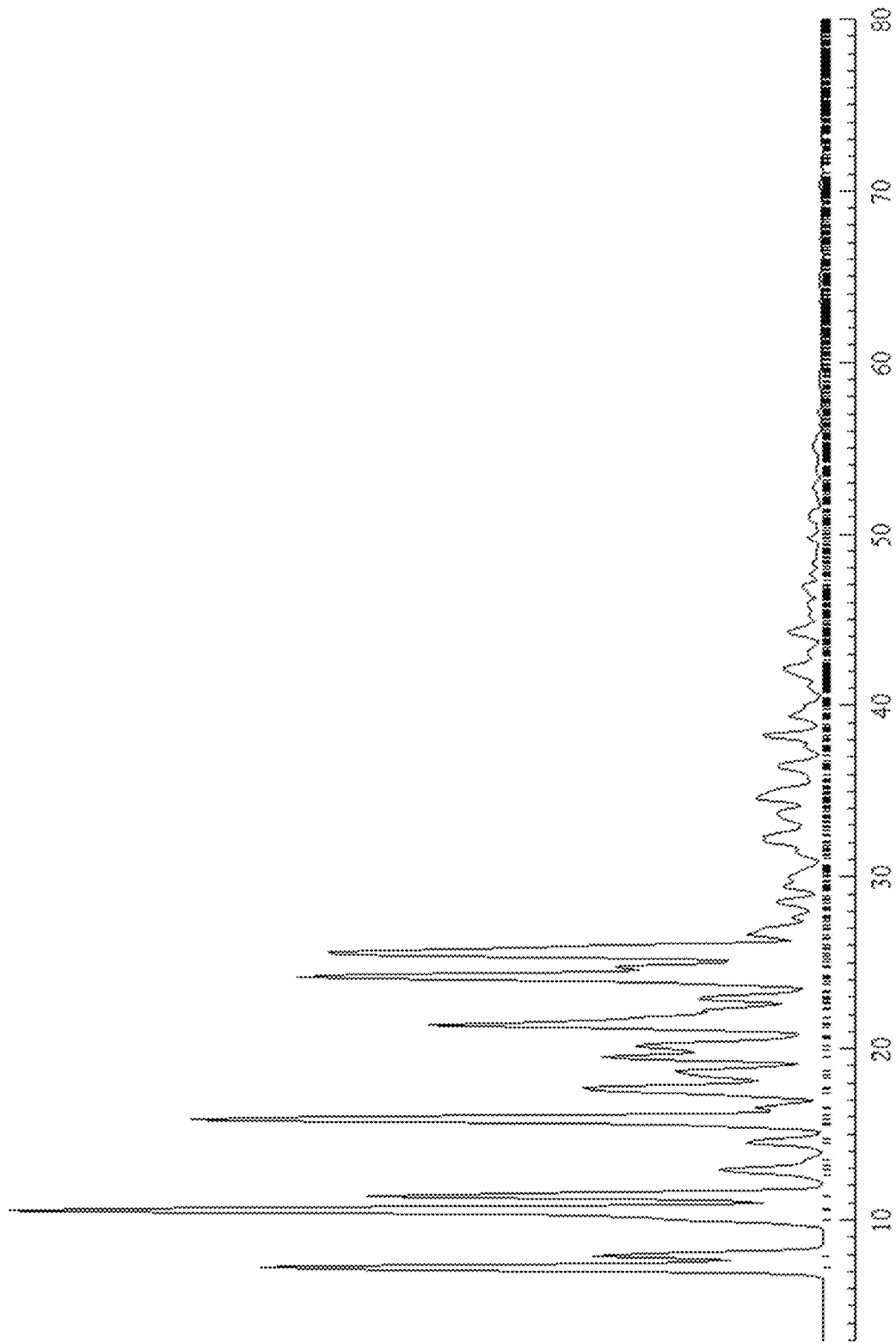
FIG. 4 is a theoretical powder X-ray diffraction spectrum of a type-B fenolamine crystal form sample (fenolamine: ethanol=2:0)
Figure 5:
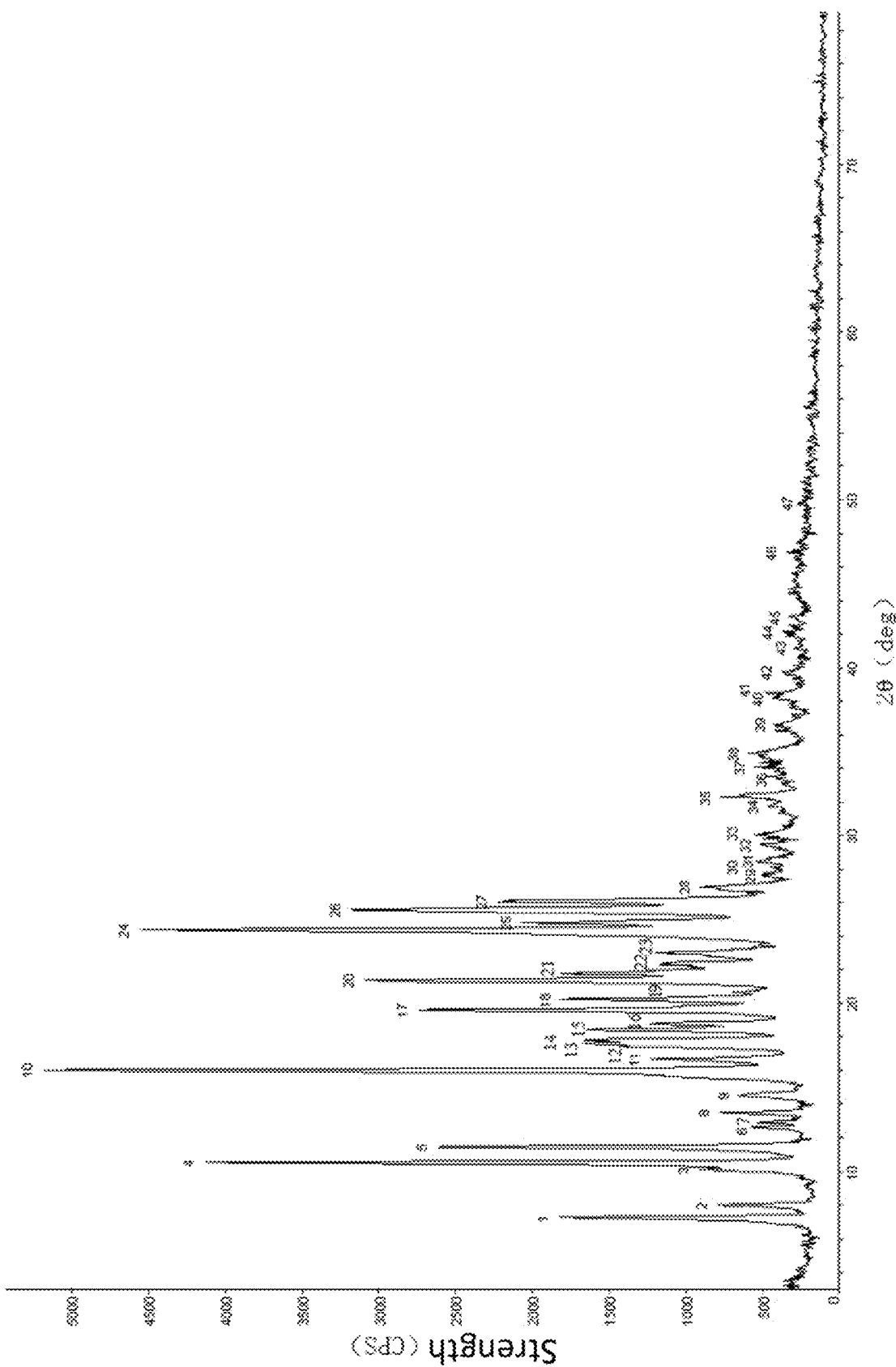
FIG. 5 is a powder X-ray diffraction spectrum of a type-B fenolamine crystal form sample.
Figure 6:
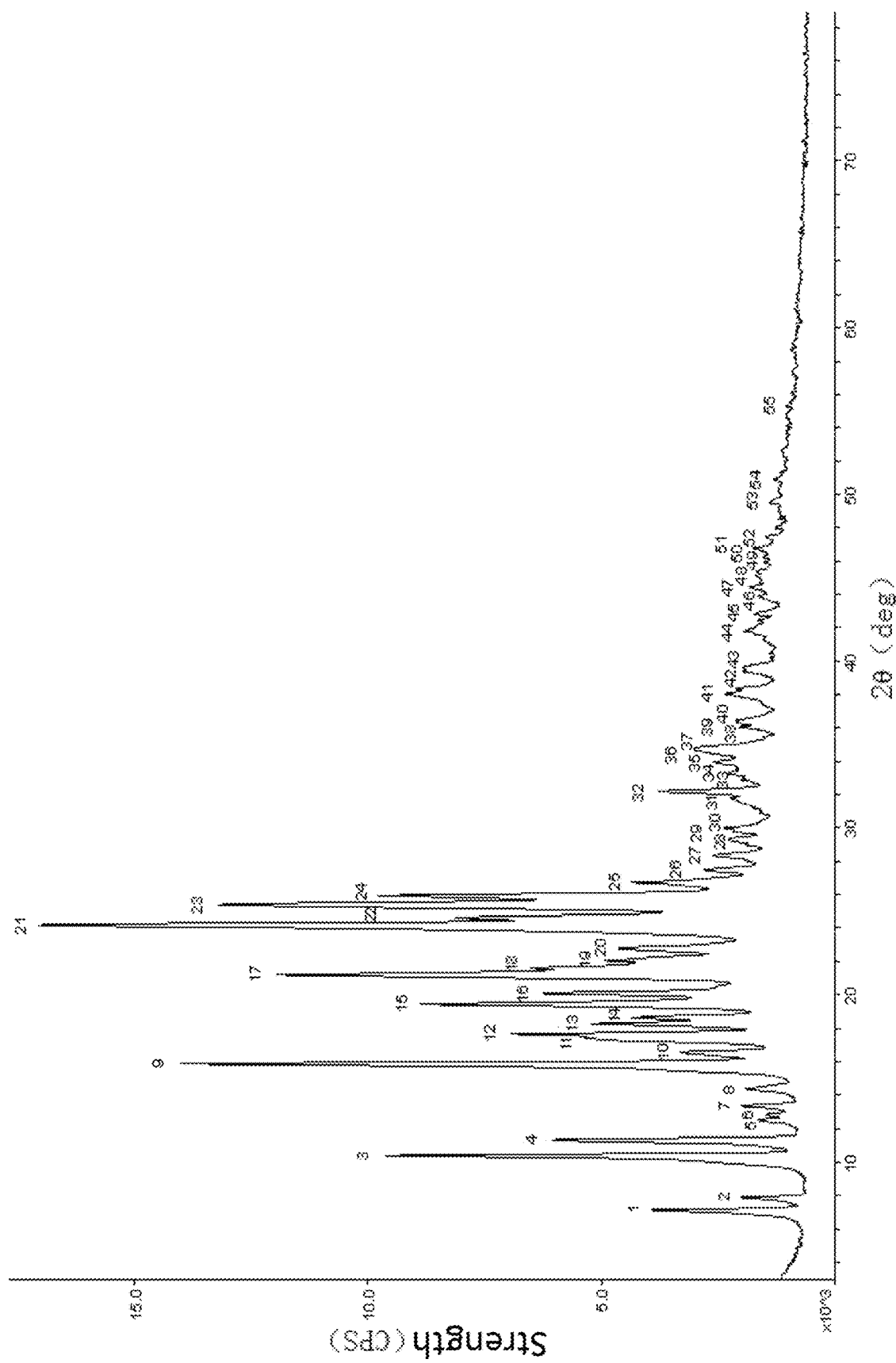
FIG. 6 is a powder X-ray diffraction spectrum of a type-B fenolamine crystal form sample.
Figure 7:
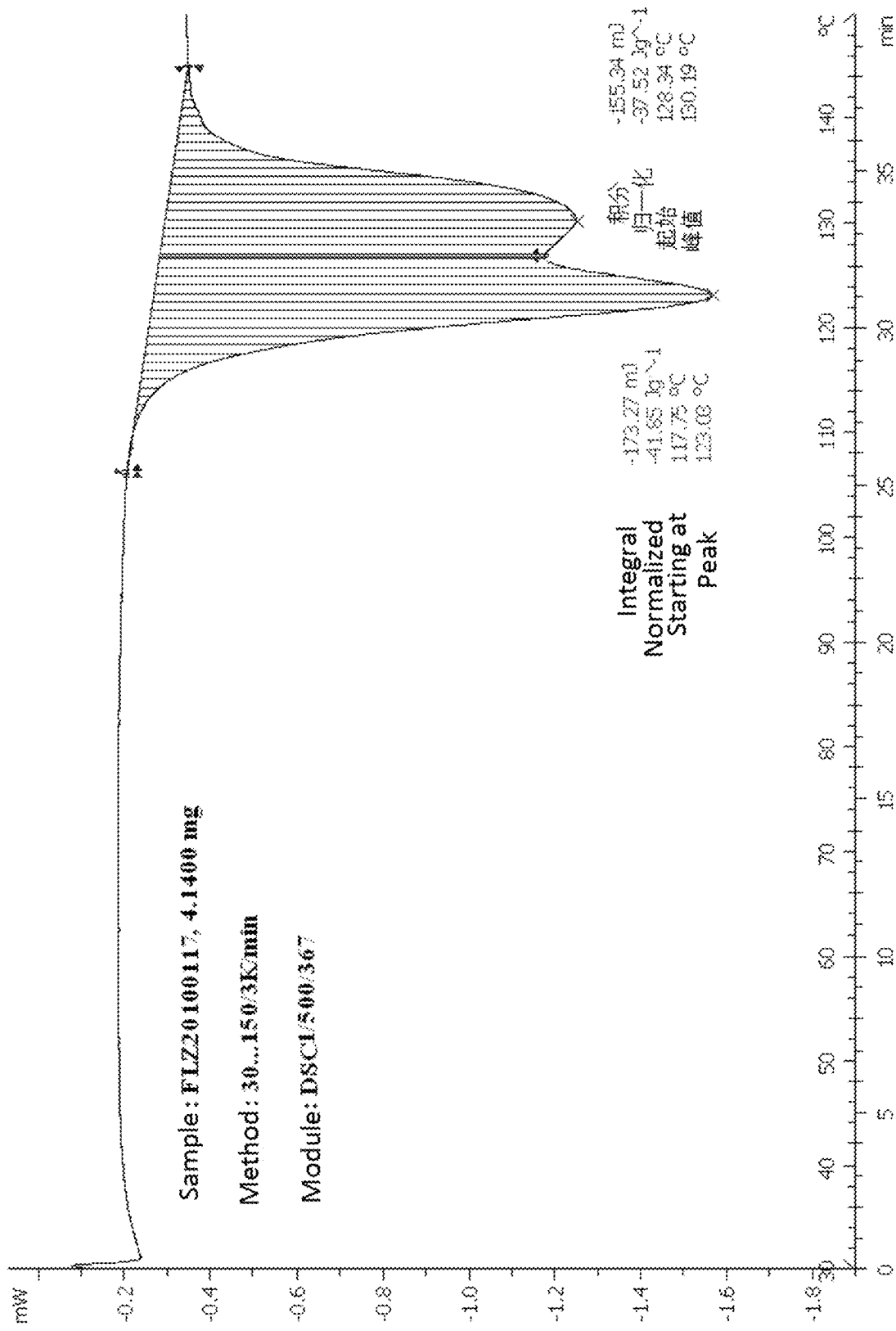
FIG. 7 is a DSC pattern of a type-B fenolamine crystal form sample.
Figure 8:
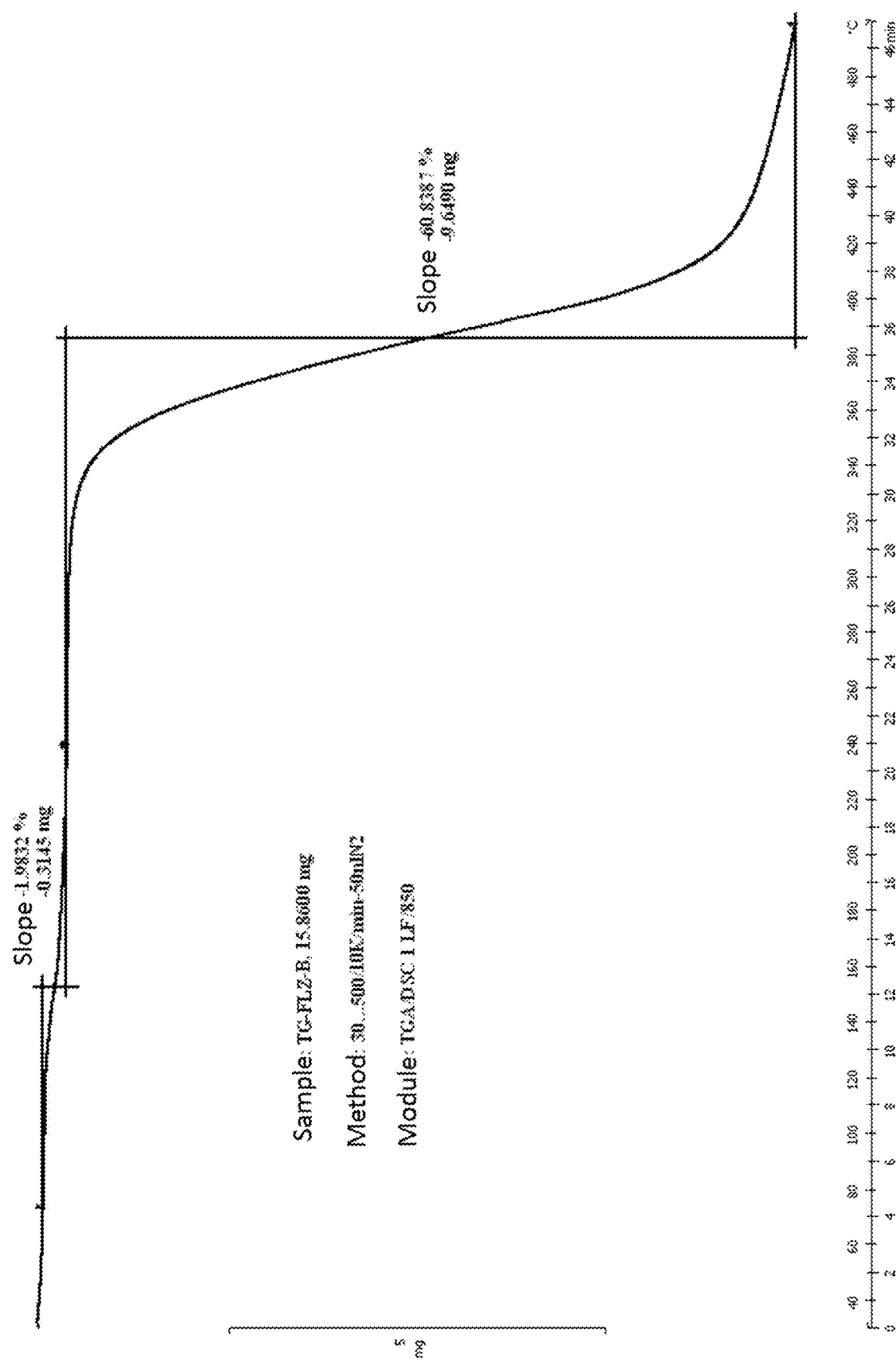
FIG. 8 is a TG diagram of type-B fenolamine crystal form sample.
Figure 9:
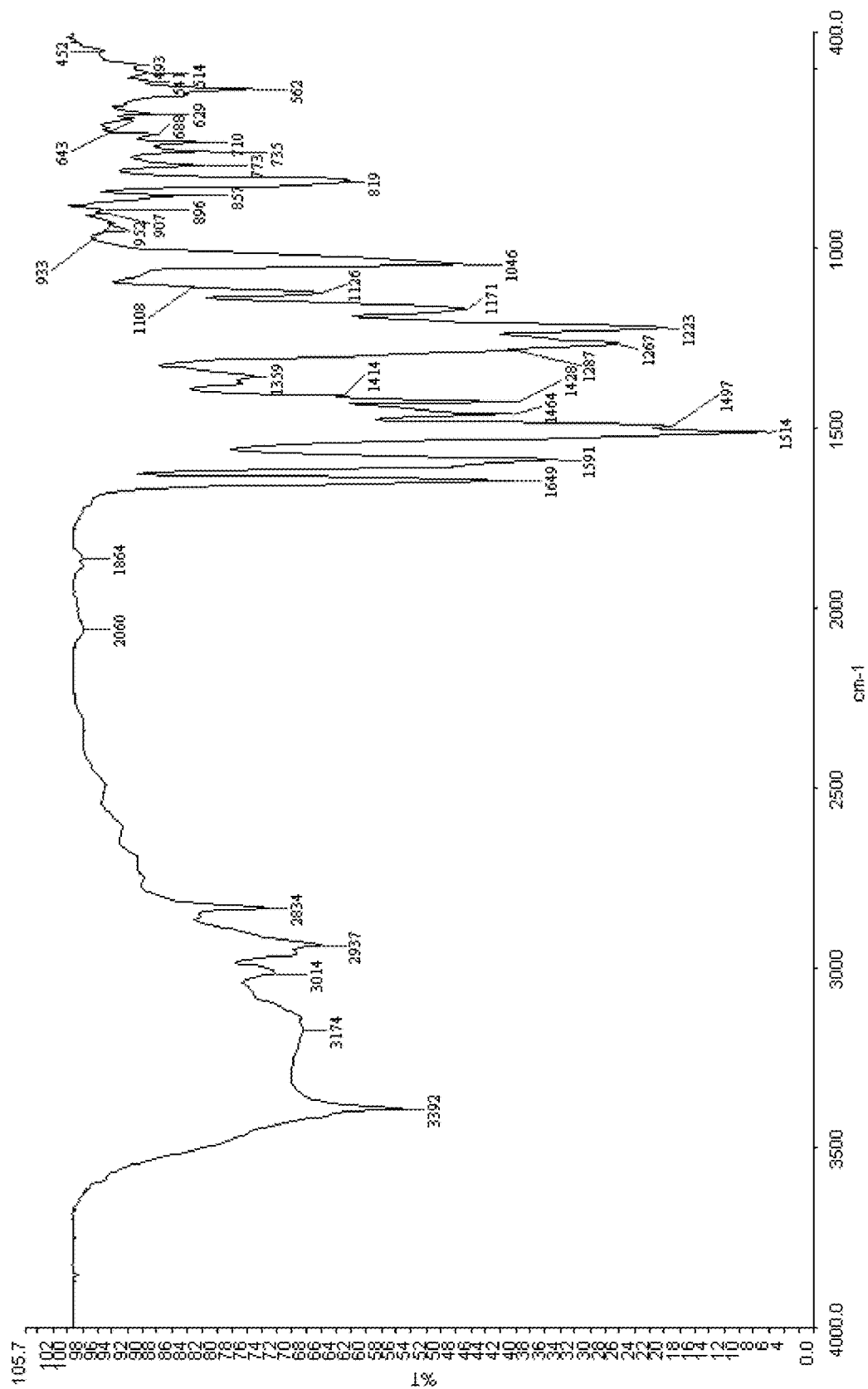
FIG. 9 is an infrared absorption spectrum of a type-B fenolamine crystal form sample.

Preparation Method 2 of Type-B Fenolamine Crystal Form Sample:

A fenolamine sample was completely dissolved in anhydrous ethanol as solvent at 40° C. and then allowed to stand at a temperature of 4 to 40° C. for 1 to 5 days so as to obtain a colorless transparent crystal of fenolamine. Single crystal X-ray diffraction analysis shows the sample has a symmetry of a monoclinic crystal system, with a Cc space group and cell parameters of: a=31.18 Å, b=8.92 Å, c=22.50 Å, α=γ=90°, β=128.4°, and an intracellular molecule number Z=8, and includes crystallized ethanol molecules in unit cells in addition to fenolamine molecules with a ratio of fenolamine to ethanol molecule of 2:1 (FIG. 1). Powder X-ray diffraction analysis was carried out, with the powder X-ray diffraction pattern shown in FIG. 6.

Preparation Method 3 of Type-B Fenolamine Crystal Form Sample:

By using a mixed solvent containing ethanol, such as a mixed solvent system having an ethanol content of 40%, 75%, or 95%, a fenolamine sample was completely dissolved at 15 to 80° C., and then allowed to stand at a temperature of 10-20° C. for 7 days so as to obtain a colorless and transparent crystal of fenolamine. Powder X-ray diffraction analysis was carried out, with an X-ray powder diffraction pattern consistent with that of FIG. 6.

By using a mixed solvent containing ethanol, such as a mixed solvent system with ethanol:methanol (2:1), a fenolamine sample was completely dissolved at 50° C., and then allowed to stand at a temperature of 20° C. for 7 days so as to obtain a colorless and transparent crystal of fenolamine. Powder X-ray diffraction analysis was carried out, with an X-ray powder diffraction pattern consistent with that of FIG. 6.

By using a mixed solvent containing ethanol, such as a mixed solvent system with ethanol:chloroform (1:1), a fenolamine sample was completely dissolved at 30° C., and then allowed to stand at a temperature of 10° C. for 10 days so as to obtain a colorless and transparent crystal of fenolamine. Powder X-ray diffraction analysis was carried out, with an X-ray powder diffraction pattern consistent with that of FIG. 6.

By using a mixed solvent containing ethanol, such as a mixed solvent system with ethanol:acetonitrile (3:1), a fenolamine sample was completely dissolved at 60° C., and then allowed to stand at a temperature of 40° C. for 5 days so as to obtain a colorless and transparent crystal of fenolamine. Powder X-ray diffraction analysis was carried out, with an X-ray powder diffraction pattern consistent with that of FIG. 6.

By using a mixed solvent containing ethanol, such as a mixed solvent system with ethanol: acetone (1:1), a fenolamine sample was completely dissolved at 20° C., and then allowed to stand at a temperature of 4° C. for 12 days so as to obtain a colorless and transparent crystal of fenolamine. Powder X-ray diffraction analysis was carried out, with an X-ray powder diffraction pattern consistent with that of FIG. 6.

By using a mixed solvent containing ethanol, such as a mixed solvent system with ethanol: cyclohexane (1:1), a fenolamine sample was completely dissolved at 20° C., and then allowed to stand at a temperature of 4° C. for 12 days so as to obtain a colorless and transparent crystal of fenolamine. Powder X-ray diffraction analysis was carried out, with an X-ray powder diffraction pattern consistent with that of FIG. 6.

The mixed solvent containing ethanol refers to a mixed solvent prepared by mixing ethanol with one or more of a single solvent system such as methanol, isopropanol, n-propanol, n-butanol, chloroform, dichloromethane, acetonitrile, tetrahydrofuran, ethyl acetate, acetone, pyridine, dioxane, glacial acetic acid, formic acid, ethyl ether, toluene, benzene, n-hexane, cyclohexane, DMF, petroleum ether, or water in arbitrary proportion, preferably with an ethanol volume ratio of greater than 40%.

Preparation Method 4 of Type-B Fenolamine Crystal Form Sample:

Materials of the type-B fenolamine crystal form subtypes having different ethanol contents were obtained by drying the type-B fenolamine crystal form subtype having an ethanol content of 5.3% under different drying conditions. The results are shown in Table 2:

TABLE 2

| Serial No. | Sample No. | Average content in ethanol (%) |
| --- | --- | --- |
| 1 | Type-B fenolamine crystal form crude drug | 5.30 |
| 2 | Type-B fenolamine crystal form crude drug dried under reduced pressure at 60° c. for 24 hours | 4.55 |
| 3 | Type-B fenolamine crystal form crude drug dried under the reduced pressure at 80° c. for 24 hours | 3.92 |

TABLE 2-continued

| Serial No. | Sample No. | Average content in ethanol (%) |
| --- | --- | --- |
| 4 | Type-B fenolamine crystal form crude drug dried under the reduced pressure at 100° c. for 12 hours | 3.57 |
| 5 | Type-B fenolamine crystal form crude drug dried under the reduced pressure at 100° c. for 24 hours | 3.76 |
| 6 | Type-B fenolamine crystal form crude drug dried under the reduced pressure at 105° c. for 4 hours | 3.71 |
| 7 | Type-B fenolamine crystal form crude drug dried under the reduced pressure at 105° c. for 12 hours | 3.66 |
| 8 | Type-B fenolamine crystal form crude drug dried under the reduced pressure at 105° c. for 24 hours | 3.45 |

Example 2

Advantageous Feature in Drug Safety of Type-B Fenolamine Crystal Form Solid

The solid of type-B fenolamine crystal form contains ethanol as crystallized solvent, which has little effect on human health, and therefore the type-B fenolamine crystal form solid has the advantageous feature in drug safety.

Example 3

Advantageous Feature in Solubility of Type-B Fenolamine Crystal Form Solid in Six Solvent Systems The solubility was evaluated by using a type-B fenolamine crystal form sample (fenolamine:ethanol=1:0.2) having a crystallized ethanol content of 2.0%.

The solvent systems were selected by: (1) referring to solvent systems used in the dissolution determination method in the Appendix of the Pharmacopoeia; (2) referring to the digestive solution pH in various organs of an organism; (3) improving the solubility of water-insoluble drugs. Based the above three references, solvent systems with six pH values were set up: a 0.1 N hydrochloric acid solution with pH 1.2; an acetate buffer solution with pH 4.5; a phosphate buffer solution with pH 6.5; an water solution with pH 6.7; a 0.2% SDS solution with pH 7.0; a 0.5% SDS solution with pH 7.3.

Figure 10:
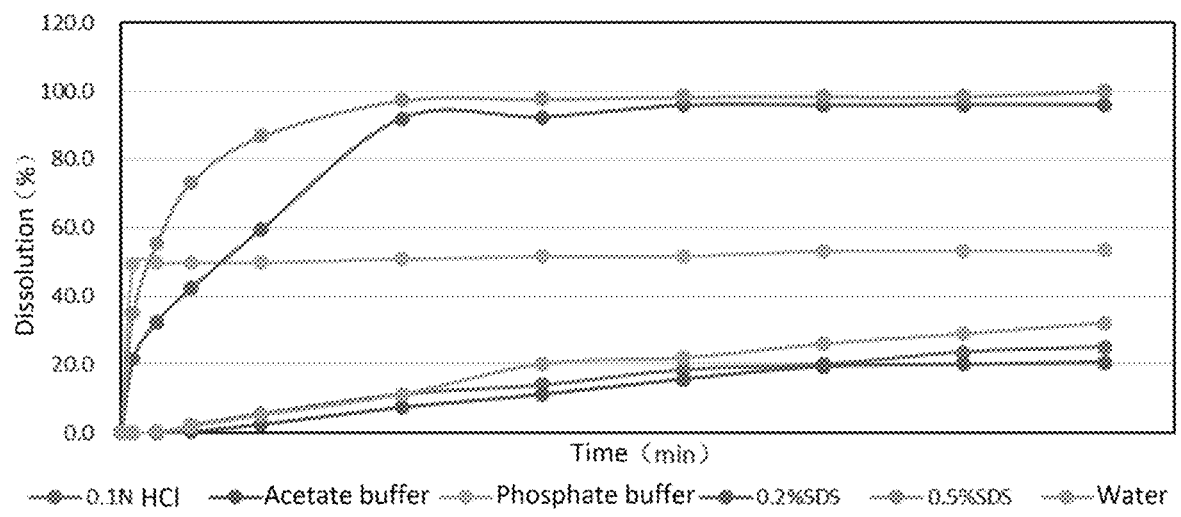
FIG. 10 is a graph of the dissolution curves of the type-B fenolamine crystal form in six different solvent systems.

Measurement was carried out according to the solubility determination method ("Guidelines for Dissolution Test Technique of General Oral Solid Preparations (Draft)", October 2012, the Drug Review Center). With the percentage of the samples dissolved by mass calculated from the absorbance data, solubility curves were respectively drawn with time as abscissa and dissolved contents as ordinate and shown in FIG. 10. The data are shown in Table 3 below:

TABLE 3

Dissolution data of type-B fenolamine crystal form in various solvent systems (%)

| Solvent Systems | Time (min) | | | | | | | | | |
| --- | --- | --- | --- | --- | --- | --- | --- | --- | --- | --- |
| | 5 | 15 | 30 | 60 | 120 | 180 | 240 | 300 | 360 | 420 |
| 0.1N hydrochloric acid | 0.00 | 0.00 | 2.35 | 5.75 | 11.42 | 14.07 | 18.54 | 20.04 | 23.69 | 25.07 |
| Acetate buffer | 0.00 | 0.00 | 0.49 | 2.57 | 7.54 | 11.34 | 15.82 | 19.51 | 20.15 | 20.71 |
| Phosphate buffer | 49.51 | 49.81 | 49.89 | 49.96 | 51.08 | 51.72 | 51.87 | 53.32 | 53.40 | 53.47 |
| 0.2% SDS | 21.57 | 32.50 | 42.43 | 59.66 | 91.98 | 92.35 | 95.75 | 95.82 | 95.90 | 95.93 |
| 0.5% SDS | 35.04 | 55.30 | 73.32 | 86.90 | 97.35 | 97.69 | 98.40 | 98.47 | 98.51 | 100.00 |
| Water | 0.00 | 0.34 | 2.01 | 5.26 | 11.42 | 20.22 | 21.94 | 26.04 | 28.96 | 32.13 |

Example 4

Stability of Type-B Fenolamine Crystal Form Solid

Type-B fenolamine crystal form samples (having a crystallized ethanol content of 2.58%) were placed in open clean watch glasses, and kept under conditions of a high temperature of 60° C., a high temperature of 40° C., and 25° C., a relative humidity of 90%±5%, and illumination at 4500 lx±500 lx for 10 days, and samples were taken on Days 0, 5, and 10. Powder X-ray diffraction (with a resultant pattern consistent to that in FIG. 1) and gas chromatography means were used for analysis. The results show that the type-B fenolamine crystal form is stable under conditions of high temperature, high humidity and light illumination, with transformation to subtypes having lower ethanol contents and a crystallized ethanol content of about 2.1% for 10 days at high temperature.

Example 5

Preparation Method 1 of Combinational Drug Preparation (Tablet):

A preparation method of a combinational drug tablet is characterized in that a pure product of type-B fenolamine crystal form or a solid of mixed crystal forms containing any ratio of the type-B crystal form used as a pharmaceutical raw material for a combinational drug, together with several excipients as adjuvant ingredients for preparing a combinational drug tablet, are used and formulated in a certain ratio into a tablet sample containing 10 to 500 mg drug per tablet. Table 4 shows the proportions in the tablet formulation:

TABLE 4

Formulations for preparing fenolamine combinational drug tablets

| Names of raw materials and excipients | Formulation 1 | Formulation 2 | Formulation 3 | Formulation 4 | Formulation 5 | Formulation 6 | Formulation 7 |
|---|---|---|---|---|---|---|---|
| Fenolamine (mg) | 10.0 | 50.0 | 100.0 | 200.0 | 250.0 | 300.0 | 500.0 |
| Lactose (mg) | q.s | q.s | q.s | q.s | q.s | q.s | q.s |
| Starch (mg) | q.s | q.s | q.s | q.s | q.s | q.s | q.s |
| Low-substituted hydroxypropyl cellulose (mg) | q.s | q.s | q.s | q.s | q.s | q.s | q.s |
| Microcrystalline cellulose (mg) | q.s | q.s | q.s | q.s | q.s | q.s | q.s |
| Talc powder (mg) | q.s | q.s | q.s | q.s | q.s | q.s | q.s |
| magnesium stearate (mg) | q.s | q.s | q.s | q.s | q.s | q.s | q.s |
| 1% sodium hydroxymethylcellulose (mg) | q.s | q.s | q.s | q.s | q.s | q.s | q.s |

The process of formulating a pure product of type-B fenolamine crystal form or a solid of mixed crystal forms containing any ratio of the type-B crystal form as a pharmaceutical raw material into a tablet preparation includes: uniformly mixing several excipients and the pharmaceutical raw material, adding an appropriate amount of a 1% sodium hydroxymethylcellulose solution to prepare a soft material, sieving and granulating, drying the wet granules, sieving the granules, adding magnesium stearate and talc powder before mixing evenly, and pressing to obtain the tablets.

Preparation Method 2 of Combinational Drug Preparation (Capsule):

A preparation method of a combinational drug capsule is characterized in that a pure product of type-B fenolamine crystal form or a solid of mixed crystal forms containing any ratio of the type-B crystal form used as a pharmaceutical raw material for a combinational drug, together with several excipients as adjuvant ingredients for preparing a combinational drug capsule, are used and formulated in a certain ratio into a capsule sample containing 10 to 500 mg drug per capsule. Table 5 shows the proportions in the capsule formulation:

TABLE 5

Formulations of raw materials and excipients for preparing fenolamine combinational drug capsule preparations

| Names of raw materials and excipients | Formulation 1 | Formulation 2 | Formulation 3 | Formulation 4 | Formulation 5 | Formulation 6 | Formulation 7 |
|---|---|---|---|---|---|---|---|
| Fenolamine (mg) | 10.0 | 50.0 | 100.0 | 200.0 | 250.0 | 300.0 | 500.0 |
| Lactose (mg) | q.s | q.s | q.s | q.s | q.s | q.s | q.s |
| Starch (mg) | q.s | q.s | q.s | q.s | q.s | q.s | q.s |
| Microcrystalline cellulose (mg) | q.s | q.s | q.s | q.s | q.s | q.s | q.s |
| Magnesium stearate (mg) | q.s | q.s | q.s | q.s | q.s | q.s | q.s |
| 1% sodium hydroxymethylcellulose (mg) | q.s | q.s | q.s | q.s | q.s | q.s | q.s |

The process of formulating a pure product of type-B fenolamine crystal form or a solid of mixed crystal forms containing any ratio of the type-B crystal form as a pharmaceutical raw material into a tablet preparation includes: uniformly mixing several excipients and the pharmaceutical raw material, adding an appropriate amount of a 1% sodium carboxymethylcellulose solution and granulating to prepare wet granules, drying and sieving the granules, adding magnesium stearate before uniformly mixing, and incorporating into a capsule. Alternatively, without the granulating step, the type-B fenolamine crystal form raw material is directly mixed with several excipients uniformly, and sieved and incorporated directly into a capsule.

Example 6

Dosage 1 for Administration of a Crystalline Fenolamine Combinational Drug (Tablet):

A pharmaceutical composition is developed and prepared by using a crystalline fenolamine sample as a pharmaceutically active ingredient, characterized in that the type-B fenolamine crystal form is used as a pharmaceutically active ingredient with a daily dose of 10 to 3000 mg, and can be prepared to be given in 1 to 6 common tablets each containing 10, 100, 200, 300, or 500 mg of the active ingredient once or twice per day, respectively.

Dosage 2 for Administration of a Crystalline Fenolamine Combinational Drug (Capsule):

A pharmaceutical composition is developed and prepared by using a crystalline fenolamine sample as a pharmaceutically active ingredient, characterized in that the type-B fenolamine crystal form is used as a pharmaceutically active ingredient with a daily dose of 10 to 3000 mg, and can be prepared to be given in 1 to 6 capsules each containing 10, 100, 200, 300, or 500 mg of the active ingredient once or twice per day, respectively.

It is noteworthy that there are many factors influencing the given dosage of the active ingredient in the crystalline fenolamine pharmaceutical composition of the present invention, for example, different daily doses resulted from different preventative or therapeutic uses; different daily doses resulted from differences in the nature of the disease and the severity of the disease; different daily doses resulted from differences in gender, age, and body surface area of the patient, the route of administration, the number of administrations, and the purpose of treatment. In addition, the absorption and blood concentration of the crystalline sample may also vary, resulting in a suitable daily dosage in the range of 0.01 to 300 mg/kg body weight, preferably 1 to 50 mg/kg body weight, for using the crystalline fenolamine component according to the present invention. According to the actual needs in the prevention and treatment of various conditions in use, different overall dosage regimens may be established which can be accomplished by giving the active ingredient of the type-B fenolamine crystal form once or several times.

The invention claimed is:

1. A solid of the type-B fenolamine crystal form, wherein the solid of the type-B fenolamine crystal form is a subtype having a ratio of fenolamine molecule to crystallized ethanol molecule of 1:0.2, and by using powder X-ray diffraction analysis under the CuKα radiation experimental conditions, has diffraction peaks at positions with 2-Theta values)(°), which include:
10.6±0.2°, 16.0±0.2°, 21.4±0.2°, 21.7±0.2°, 24.4±0.2° and 25.6±0.2°.

2. The solid of the type-B fenolamine crystal form according to claim 1, wherein by using differential scanning calorimetry analysis, one endothermic peak at 123° C.±3° C. and one at 130° C.±3° C. are present respectively in the DSC pattern thereof in a range of 30 to 150° C. and at a heating rate of 3° C. per minute.

3. The solid of the type-B fenolamine crystal form according to claim 1, wherein by using attenuated total reflection Fourier infrared spectroscopy analysis, IR characteristic peaks are present at 3392, 3174, 3014, 2937, 2834, 2060, 1864, 1649, 1591, 1514, 1497, 1464, 1428, 1414, 1359, 1287, 1267, 1223, 1171, 1126, 1108, 1046, 952, 933, 907, 896, 857, 819, 773, 735, 710, 688, 643, 629, 562, 541, 514, 493, 452 cm-1, and wherein the allowable deviation of the IR characteristic peaks is ±2 cm$^{-1}$.

4. A preparation method for the solid of the type-B fenolamine crystal form according to claim 1, wherein the solid of the type-B fenolamine crystal form is prepared by dissolving a fenolamine material completely with ethanol as sole solvent or a mixed solvent containing ethanol at a temperature of 15° C. to 80° C., followed by recrystallization at ambient temperature of 4° C. to 80° C. and ambient humidity of 10% to 75% under normal pressure or vacuum conditions.

5. The preparation method according to claim 4, wherein the mixed solvent containing ethanol has an ethanol content by mass of more than or equal to 40%.

6. A solid of mixed fenolamine crystal forms, wherein the solid of the type-B fenolamine crystal form according to claim 1 is comprised in an amount of 1% to 99.9%.

7. A pharmaceutical composition, wherein the composition comprises an effective amount of the solid of the type-B fenolamine crystal form according to claim 1, and a pharmaceutically acceptable carrier.

8. The pharmaceutical composition according to claim 7, wherein daily dose of fenolamine is in the range of 10 to 3000 mg.

9. The pharmaceutical composition according to claim 7, wherein the pharmaceutical composition is in a dosage form of a tablet, a capsule, a pill, an injection, a sustained release preparation, or a controlled release preparation, and is in a solid dosage form.

10. The preparation method according to claim 5, wherein the mixed solvent containing ethanol is a mixed solvent of ethanol and at least one solvent selected from methanol, isopropanol, n-propanol, n-butanol, chloroform, dichloromethane, acetonitrile, tetrahydrofuran, ethyl acetate, acetone, pyridine, dioxane, glacial acetic acid, formic acid, ethyl ether, toluene, benzene, n-hexane, cyclohexane, DMF, petroleum ether, and water.

11. The solid of mixed fenolamine crystal forms according to claim 6, wherein the type-B fenolamine crystal form is comprised in an amount of 10% to 99.99%.

12. The solid of mixed fenolamine crystal forms according to claim 6, wherein the type-B fenolamine crystal form is comprised in an amount of 50% to 99.9%.

13. The solid of mixed fenolamine crystal forms according to claim 6, wherein the type-B fenolamine crystal form is comprised in an amount of 90% to 99.9%.

14. A pharmaceutical composition, wherein the composition comprises an effective amount of the solid of mixed fenolamine crystal forms according to claim 6 and a pharmaceutically acceptable carrier.

15. A method for treatment of Parkinson's disease, wherein the method comprises administering the solid of the type-B fenolamine crystal form according to claim 1.

16. A method for treatment of Parkinson's disease, wherein the method comprises administering the solid of mixed fenolamine crystal forms according to claim 6.

17. A method for treatment of Parkinson's disease, wherein the method comprises administering the pharmaceutical composition according to claim 7.

18. A method for treatment of Parkinson's disease, wherein the method comprises administering the solid of mixed fenolamine crystal forms according to claim 12.

19. The solid of a type-B fenolamine crystal form according to claim 1, wherein the type-B crystal form shows a symmetry of a monoclinic crystal system upon single crystal X-ray diffraction analysis, with a Cc space group and unit cell parameters of: a=31.18 Å, b=8.92 Å, c=22.50 Å, α=γ=90°, β3=128.4°, and an intracellular molecule number Z=8, and includes crystallized ethanol molecules in unit cells in addition to fenolamine molecules.

20. A solid of type-B fenolamine crystal forms comprising the type-B crystal form according to claim 1 and at least one other subtype of a type-B fenolamine crystal form, wherein the ratio of fenolamine molecule to crystallized ethanol molecule in the type-B fenolamine crystal forms is within the range of 1:0.5 to 1:0.1.

21. The solid of the type-B fenolamine crystal forms according to claim 20, wherein the at least one other subtype is a subtype, which has a ratio of fenolamine molecule to crystallized ethanol molecule of 1:0.5.

22. The solid of the type-B fenolamine crystal form according to claim 1, wherein by using differential scanning calorimetry analysis, a weight loss peak is present in the range of 100 to 150° C. with a weight loss of 1.5% to 5.0%.

23. The solid of a type-B fenolamine crystal form according to claim 1, wherein by using powder X-ray diffraction analysis under the CuKα radiation experimental conditions, the solid of the type-B fenolamine crystal form subtype has diffraction peaks at positions with 2-Theta values)(°) or d values (Å) and diffraction peaks with relative intensity peak height values (Height %) or peak area values (Area %) as shown below:

| Peak | 2-Theta ± 0.2° | d(Å) ± 0.2 Å | Height % ± 10% | Area % ± 10% |
|---|---|---|---|---|
| 1 | 7.3 | 12.1 | 34 | 28 |
| 2 | 8.0 | 11.0 | 12 | 8 |
| 3 | 10.1 | 8.7 | 14 | 17 |

-continued

| Peak | 2-Theta ± 0.2° | d(Å) ± 0.2 Å | Height % ± 10% | Area % ± 10% |
|---|---|---|---|---|
| 4 | 10.6 | 8.4 | 79 | 62 |
| 5 | 11.5 | 7.7 | 48 | 38 |
| 6 | 12.7 | 7.0 | 6 | 6 |
| 7 | 12.9 | 6.8 | 6 | 6 |
| 8 | 13.5 | 6.5 | 11 | 6 |
| 9 | 14.5 | 6.1 | 9 | 9 |
| 10 | 16.0 | 5.5 | 100 | 100 |
| 11 | 16.7 | 5.3 | 16 | 10 |
| 12 | 17.4 | 5.1 | 21 | 32 |
| 13 | 17.6 | 5.0 | 25 | 40 |
| 14 | 17.8 | 5.0 | 25 | 44 |
| 15 | 18.4 | 4.8 | 24 | 19 |
| 16 | 18.8 | 4.7 | 16 | 15 |
| 17 | 19.6 | 4.5 | 46 | 36 |
| 18 | 20.2 | 4.4 | 27 | 24 |
| 19 | 20.7 | 4.3 | 3 | 1 |
| 20 | 21.4 | 4.2 | 50 | 46 |
| 21 | 21.7 | 4.1 | 26 | 48 |
| 22 | 22.3 | 4.0 | 6 | 2 |
| 23 | 23.0 | 3.9 | 13 | 11 |
| 24 | 24.4 | 3.7 | 81 | 95 |
| 25 | 24.8 | 3.6 | 27 | 23 |
| 26 | 25.6 | 3.5 | 51 | 60 |

-continued

| Peak | 2-Theta ± 0.2° | d(Å) ± 0.2 Å | Height % ± 10% | Area % ± 10% |
|---|---|---|---|---|
| 27 | 26.1 | 3.4 | 33 | 32 |
| 28 | 26.9 | 3.3 | 9 | 7 |
| 29 | 27.6 | 3.2 | 3 | 3 |
| 30 | 27.8 | 3.2 | 3 | 3 |
| 31 | 28.4 | 3.1 | 4 | 6 |
| 32 | 29.5 | 3.0 | 4 | 3 |
| 33 | 30.0 | 3.0 | 4 | 5 |
| 34 | 31.8 | 2.8 | 4 | 9 |
| 35 | 32.3 | 2.8 | 10 | 12 |
| 36 | 33.4 | 2.7 | 1 | 1 |
| 37 | 34.1 | 2.6 | 3 | 1 |
| 38 | 34.9 | 2.6 | 5 | 8 |
| 39 | 36.6 | 2.5 | 4 | 8 |
| 40 | 38.2 | 2.4 | 4 | 8 |
| 41 | 38.5 | 2.3 | 5 | 7 |
| 42 | 39.7 | 2.3 | 3 | 4 |
| 43 | 41.2 | 2.2 | 1 | 2 |
| 44 | 42.1 | 2.1 | 3 | 3 |
| 45 | 43.1 | 2.1 | 2 | 1 |
| 46 | 46.9 | 1.9 | 2 | 2 |
| 47 | 49.9 | 1.8 | 1 | 1 |

\* \* \* \* \*